United States Patent
Tucker et al.

(10) Patent No.: US 11,185,524 B2
(45) Date of Patent: Nov. 30, 2021

(54) MEANS FOR PROTECTING METHIONINE HYDROXY ANALOG FROM RUMEN DEGRADATION

(71) Applicant: Novus International, Inc., St. Charles, MO (US)

(72) Inventors: Heather A. Tucker, St. Charles, MO (US); Matthew Mahoney, St. Charles, MO (US); Tracy M. Rode, St. Charles, MO (US); Jason Schultz, St. Charles, MO (US); Mercedes Vázquez-Añón, St. Charles, MO (US); William Scott Hine, St. Charles, MO (US)

(73) Assignee: Novus International, Inc., St. Charles, MO (US)

( * ) Notice: Subject to any disclaimer, the term of this patent is extended or adjusted under 35 U.S.C. 154(b) by 0 days.

(21) Appl. No.: 16/412,634

(22) Filed: May 15, 2019

(65) Prior Publication Data

US 2020/0360333 A1    Nov. 19, 2020

(51) Int. Cl.
| | | |
|---|---|---|
| *A61K 31/23* | (2006.01) | |
| *A23K 20/158* | (2016.01) | |
| *A23K 50/15* | (2016.01) | |
| *A61P 1/00* | (2006.01) | |

(52) U.S. Cl.
CPC ............ *A61K 31/23* (2013.01); *A23K 20/158* (2016.05); *A23K 50/15* (2016.05); *A61P 1/00* (2018.01)

(58) Field of Classification Search
CPC .... A23K 31/23; A23K 31/215; A23K 31/231; A23K 20/158; A23K 20/105; A23K 50/15
See application file for complete search history.

(56) References Cited

U.S. PATENT DOCUMENTS

| | | |
|---|---|---|
| 3,959,493 A | 5/1976 | Baalsrud |
| 6,017,563 A | 1/2000 | Knight |
| 9,169,203 B2 | 10/2015 | Grady |
| 10,106,496 B2 | 10/2018 | Mahoney |
| 2002/0110589 A1 | 8/2002 | Kim |
| 2017/0000755 A1 | 1/2017 | Arhancet |

OTHER PUBLICATIONS

International Search Report and Written Opinion dated Jul. 2, 2020 in related international application No. PCT/US2020/031317, 10 pp.
Chen, Z. H., G. A. Broderick, N. D. Luchini, B. K. Sloan, and E. Devillard. 2011. Effect of feeding different sources of rumen-protected methionine on milk production and N-utilization in lactating dairy cows. J. Dairy Sci. 94: 1978-1988.
Koenig, K. M., L. M. Rode, C. D. Knight, and P. R. McCullough. 1999. Ruminal escape, gastrointestinal absorption, and response of serum methionine to supplementation of liquid methionine hydroxy analog in dairy cows. J. Dairy Sci 82:355-361.
Noftsger, S., N. R. St-Pierre, and J. T. Sylvester. 2005. Determination of rumen degradability and ruminal effects of three sources of methionine in lactating cows. J. Dairy Sci. 88:223-237.
Papas, A. M., C. J. Sniffen, T. V. Muscato. 1984. Effectiveness of rumen-protected methionine for delivering methionine postruminally in dairy cows. J. Dairy Sci. 67: 545-552.
Patterson, J.A., and L. Kung Jr. 1988. Metabolism of DL-methionine and methionine analogs by rumen microorganisms. J. Dairy Sci. 71: 3292-3301.
Polan, C. E., K. A. Cummins, C. J. Sniffen, T. V. Muscato, J. L. Vicini, B. A. Crooker, J. H. Clark, D. G. Johnson, D. E. Otterby, B. Guillaume, L. D. Muller, G. A. Varga, R. A. Murray, and S. B. Peirce-Sandner. 1991. Responses of dairy cows to supplemental rumen-protected forms of methionine and lysine. J. Dairy Sci. 74: 2997-3013.

*Primary Examiner* — Irina Neagu
(74) *Attorney, Agent, or Firm* — Polsinelli PC

(57) ABSTRACT

Chemically modified methionine hydroxy analogs that are protected from degradation by rumen microorganisms. The chemically modified compounds comprise methionine hydroxy analog chemically linked to a fatty acid having at least 12 carbon atoms. Methods for increasing rumen bypass of methionine hydroxy analog and/or providing methionine hydroxy analog to a ruminant's small intestine for absorption, wherein the methods comprise administering to the ruminant a chemically modified methionine hydroxy analog as defined above.

15 Claims, No Drawings

MEANS FOR PROTECTING METHIONINE HYDROXY ANALOG FROM RUMEN DEGRADATION

FIELD

The present disclosure relates to chemically modified methionine hydroxy analogs that are protected from degradation by rumen microorganisms.

BACKGROUND

With the increased costs of protein, the dairy industry is moving toward lowering dietary protein levels and supplementing limiting amino acids to better meet the needs for milk protein synthesis. Methionine, a limiting amino acid, has been shown previously to increase milk protein, a component of milk that dairy farmers are compensated for. Free methionine cannot be fed to ruminants as the microbial community in the rumen often consumes and degrades the essential amino acid, rendering it unavailable to the cow. Therefore, the delivery of methionine or it's analog, 2-hydroxy-4-methylthio-butanoic acid (HMTBa), protected against rumen degradation, for absorption in the small intestine, is an objective for many dairy nutritionists as milk protein increases with increased plasma methionine.

Means to protect methionine or its analogs from rumen degradation include physical protection or chemical protection. Physical protection relies on other materials to encapsulate a core of methionine or HMTBa. This protection must be sensitive to neutral and low pH or thick enough to not be completely degraded by rumen microorganisms. However, the coating must not be so thick that intestinal enzymes or low pH of the abomasum cannot degrade the coating, allowing the core to be released for absorption. Chemical protection involves a modification to the chemical formulation of methionine that renders the molecule unrecognizable or not useable to the rumen microorganisms allowing for rumen bypass. This modified compound, however, must then be able to be converted into a form that allows for absorption and biological activity.

SUMMARY

Among the various aspects of the present disclosure are methods for increasing rumen bypass of methionine hydroxy analog in a ruminant. The methods comprise administering to the ruminant a chemically modified methionine hydroxy analog, the chemically modified methionine hydroxy analog comprising a methionine hydroxy analog linked by an ester bond to an aliphatic chain having at least 12 carbon atoms.

A further aspect of the present disclosure encompasses methods for providing methionine hydroxy analog to a ruminant's small intestine for absorption. The methods comprise administering to the ruminant an effective amount of a chemically modified methionine hydroxy analog, the chemically modified methionine hydroxy analog comprising a methionine hydroxy analog linked by an ester bond to an aliphatic chain having at least 12 carbon atoms.

Other aspects and features of the present disclosure are described in more detail below.

DETAILED DESCRIPTION

The present disclosure provides chemically modified compounds comprising an aliphatic chain having at least 12 carbon atoms linked by an ester bond to a methionine hydroxy analog. The chemically modified methionine analogs are protected from degradation by microorganisms in the rumen and pass through the rumen substantially intact. The ester bond linking the aliphatic chain to methionine analog, however, is hydrolyzed by the low pH of the abomasum and/or enzymes of the intestine, thereby making free methionine hydroxy analog available for absorption. Also provided are methods for increasing rumen bypass of methionine hydroxy analog and/or providing methionine hydroxy analog to a ruminant's small intestine for absorption, wherein the methods comprises administering to the ruminant a chemically modified methionine hydroxy analog as described above.

(I) Rumen Protected Methionine Analog

One aspect of the present disclosure encompasses a chemically modified methionine hydroxy analog that is protected from degradation by rumen microorganisms. The chemically modified methionine hydroxy analog comprising a methionine hydroxy analog linked to an aliphatic chain having at least 12 carbon atoms.

The aliphatic chain may be linked to the oxygen of the hydroxyl group of the carboxyl group of the methionine hydroxy analog. That is, the chemically modified methionine hydroxy acid may be a hydroxy ester of Formula (I):

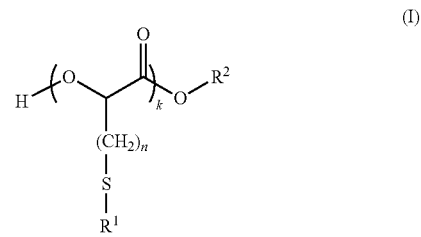

(I)

wherein:
$R^1$ is alkyl or substituted alkyl
$R^2$ is aliphatic have at least 12 carbon atoms;
n is an integer of 1 or greater; and
k is an integer of 1 or greater.

Alternatively, the aliphatic chain may be linked by an ester bond to the oxygen of the hydroxyl group of the alpha carbon of the methionine hydroxy analog. The chemically methionine hydroxy acid may be an alpha ester carboxylic acid of Formula (II):

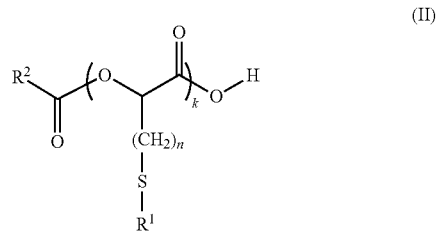

(II)

wherein:
$R^1$ is alkyl or substituted alkyl
$R^2$ is aliphatic have at least 12 carbon atoms;
n is an integer of 1 or greater; and
k is an integer of 1 or greater.

In some embodiments, $R^1$ may be $C_1$ to $C_6$ alkyl or $C_1$ to $C_6$ substituted alkyl. The alkyl may be straight chain or branched. The substituted alkyl comprises a replacement of one or more carbon and/or hydrogen atoms with a nitrogen, oxygen, phosphorous, or halogen heteroatom. In various embodiments, $R^1$ may be methyl, ethyl, propyl, isopropyl, butyl, tert-butyl, hexyl, and the like. In other embodiments, $R^1$ may be methyl or ethyl. In specific embodiments, $R^1$ may be methyl.

In various embodiments, $R^2$ may be alkyl or alkenyl having from 12 to 36 carbon atoms. In some embodiments, $R^2$ may be $C_{12}$ to $C_{30}$ alkyl or $C_{12}$ to $C_{30}$ alkenyl. In certain embodiments, $R^2$ may be derived from lauric acid, myristic acid, myristoleic acid, palmitic acid, palmitoleic acid, sapienic acid, stearic acid, oleic acid, elaidic acid, vaccenic acid, linoleic acid, linoelaidic acid, α-linolenic acid, arachidic acid, arachidonic acid, behenic acid, erucic acid, docosahexanenoic acid, lignoceric acid, cerotic acid, or a very long-chain fatty acid. In certain embodiments, $R^2$ may be $C_{14}$ alkyl or alkenyl, $C_{16}$ alkyl or alkenyl, $C_{18}$ alkyl or alkenyl, $C_{20}$ alkyl or alkenyl, $C_{22}$ alkyl or alkenyl, $C_{24}$ alkyl or alkenyl, or $C_{26}$ alkyl or alkenyl.

In certain embodiments, n may range from 1 to 10. In other embodiments, n may be 1, 2, 3, 4, or 5. In specific embodiments, n may be 1, 2, or 3. In particular embodiments, n may be 2.

In general, k may range from 1 to about 100. In certain embodiments, k may range from 1 to about 50, from 1 to about 25, from 1 to about 20, from 1 to about 15, from 1 to about 10, from 1 to 9, from 1 to 8, from 1 to 7, from 1 to 6, from 1 to 5, from 1 to 4, from 1 to 3, or from 1 to 2. In some embodiments, k may be the same in every compound (e.g., k may be 1, k may be 2, and so forth). In other embodiments, k may vary and the compound comprises a distribution of molecules (e.g., k may be 1-3, 1-5, 1-10, 1-20, and so forth). In such embodiments, the compounds of Formula (I) and Formula (II) comprise a mixture of monomers, dimers, trimers, tetramers, pentamers, hexamers, etc.

The compounds of Formula (I) or Formula (II) may have at least one chiral center, as denoted with an asterisk in each schematic below:

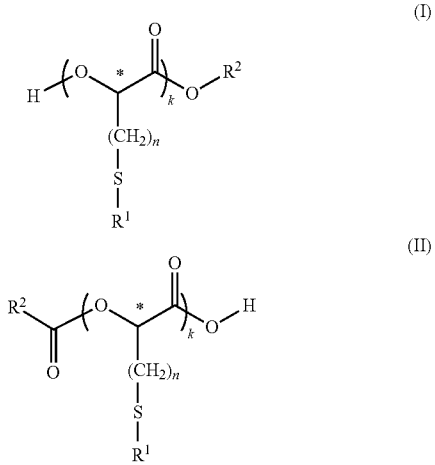

wherein $R^1$, $R^2$, k, and n are as defined above. Each chiral center may have an R or an S configuration. In compounds comprising one chiral carbon, the configuration may be R or S. In compounds comprising two or more chiral carbons, the configuration of each will be independently R or S. For example, in compounds comprising two chiral carbons, the configuration may be RR, RS, SR, or SS, in compounds comprising three chiral carbons, the configuration may be RRR, RRS, RSR, RSS, SRR, SRS, SSR, or SSS, and so forth.

In specific embodiments, $R^1$ is methyl, n is 2, k is from 1 to 10, and $R^2$ is $C_{16}$ alkyl or alkenyl, $C_{18}$ alkyl or alkenyl, or $C_{20}$ alkyl or alkenyl.

The compounds of Formula (I) or Formula (II) may be prepared as described in U.S. Pat. Nos. 9,801,845, 9,169,203, and 10,106,496, wherein the disclosure of each is incorporated by reference in its entirety.

(II) Methods for Increasing Rumen Bypass of Methionine Analog and/or Providing Methionine Analog to Ruminant's Intestine for Absorption A further aspect of the present disclosure provide methods for increasing rumen bypass of methionine analog and/or providing methionine analog to a ruminant's intestine for absorption. The methods comprise administering to the ruminant a chemically modified methionine hydroxy analog, which is described above in section (I). The chemically modified methionine hydroxy analog resists degradation by microorganism in the rumen. After passage from the rumen, the ester linkage of the chemically modified hydroxy modified methionine hydroxy analog is cleaved by the low abomasum pH and/or intestinal enzymes, thereby providing free methionine hydroxy analog that is available for absorption in the intestine.

In general, the chemically modified methionine hydroxy analog has a ruminal undegradability of at least about 60%. In some embodiments, the ruminal undegradability of the chemically modified methionine hydroxy analog is at least about 65%, at least about 70%, at least about 75%, at least about 80%, at least about 85%, or at least about 90%. Stated another way, at least about 60%, at least about 65%, at least about 70%, at least about 75%, at least about 80%, at least about 85%, or at least about 90% the chemically modified methionine hydroxy analog survives the rumen and is passed to the lower compartments of the stomach and the intestine.

An effective amount of the chemically modified methionine hydroxy analog may be administered to the ruminant as part of the animal's daily feed ration. Feed rations typically are formulated to meet the nutrient and energy demands of particular animals. The National Research Council has published books that contain tables of common ruminant feed ingredients and their respective measured nutrient and energy content. Additionally, estimates of nutrient and maintenance energy requirements are provided for growing and finishing cattle according to the weight of the cattle. National Academy of Sciences, Nutrient Requirements of Beef Cattle, Appendix Tables 1-19, 192-214, (National Academy Press, 2000); Nutrient Requirements of Dairy Cattle (2001), which are each incorporated herein by their entirety. This information can be utilized by one skilled in the art to estimate the nutritional and maintenance energy requirements of the animal and determine the nutrient and energy content of animal feed ingredients.

In the dairy and beef industry, cattle typically are fed a ration, commonly referred to as a total mixed ration (TMR), which consists of a forage portion and a grain concentrate portion. The forage portion typically comprises haylage and/or silage, and the grain concentrate portion comprises grains such as corn, oats, and/or soy. The grain concentrate portion may be prepared by a commercial feed mill, wherein the concentrate is prepared by mixing grains such as corn, soy, and alfalfa with vitamins, minerals, molasses, fat sources, synthetic amino acids, and a variety of other feedstuffs. These ingredients are blended using conventional milling techniques which include augering, mixing, expanding, extruding, and pelleting.

In some embodiments, the chemically modified methionine hydroxy analog may be added to and mixed with the grain concentrate portion of the feed ration. In other embodiments, the chemically modified methionine hydroxy analog may be added to and/or mixed with the feed ration as a feed premix or feed supplement, examples of which are described below in section (III).

Suitable ruminants include livestock ruminants such as dairy cattle (e.g., dairy cows), beef cattle (e.g., steers, heifers), sheep, or goat. In specific embodiments, the ruminant may be a dairy cow.

Ruminants administered the chemically modified methionine hydroxy analog may have increased plasma levels of methionine and methionine hydroxy analog (e.g., methionine bioequivalent) than ruminants administered a methionine hydroxy analog that is not linked to a long aliphatic chain (see Example 2 below).

Lactating dairy cows administered the chemically modified methionine hydroxy analog may have increased levels of milk protein as compared to those not administered the chemically modified methionine hydroxy analog. The milk protein content may be increased from about 0.1% to about 3.0%. In some embodiments, the milk protein content may be increased from about 0.1% to about 0.5%, from about 0.5% to about 1.0%, from about 1.0% to about 1.5%, from about 1.5% to about 2.0%, from about 2.0% to about 2.5%, or from about 2.5% to about 3.0%.

In further embodiments, lactating dairy cows administered the chemically modified methionine hydroxy analog may have increased milk protein to milk fat ratios, increased levels of milk production, increased milk yield, and/or increased milk efficiency as compared to animals not administered the chemically modified methionine hydroxy analog. In still other embodiments, ruminants administered the chemically modified methionine hydroxy analog may have improved performance parameters including weight gain, feed to gain ratio, feed conversion ratio, carcass quality, carcass yield, meat grade, meat yield, meat protein to fat ratio, and the like as compared to animals not administered the chemically modified methionine hydroxy analog.

(III) Feed Premix or Feed Supplement

A further aspect of the present disclosure encompasses animal feed premixes or feed supplements comprising at least one of the chemically modified methionine hydroxy analogs described above in Section (I). The feed premix or feed supplement may be added to various feed formulations to formulate animal feed rations, as described above in Section (II). As will be appreciated by the skilled artisan, the particular premix or supplement can and will vary depending upon the feed ration and animal that the feed ration will be fed to. Accordingly, the premix or supplement may comprise a chemically modified methionine hydroxy analog and at least one additional agent.

Examples of suitable additional agents include vitamins, minerals, amino, antioxidants, organic acids, polyunsaturated fatty acids, essential oils, enzymes, prebiotics, probiotics, herbs, pigments, nutritive agents, excipients, or combinations thereof.

In some embodiments, the feed premix or feed supplement may further comprise one or more vitamins. Suitable vitamins include vitamin A, vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid), vitamin B12, vitamin C, vitamin D, vitamin E, vitamin K, other B-complex vitamins (e.g., choline, carnitine, adenine), or combinations thereof. The form of the vitamin may include salts of the vitamin, derivatives of the vitamin, compounds having the same or similar activity of a vitamin, and metabolites of a vitamin.

In other embodiments, the feed premix or feed supplement may further comprise one or more minerals. Examples of suitable minerals include calcium, chromium, cobalt, copper, iodine, magnesium, manganese, molybdenum, selenium, zinc, or combinations thereof. The mineral may be an inorganic mineral. Suitable inorganic minerals include, for example, metal sulfates, metal oxides, metal hydroxides, metal oxychlorides, metal carbonates, and metal halides. Alternatively, the mineral may be an organic mineral, e.g., a metal chelate comprising a metal ion and an organic ligand. The organic ligand may be an amino acid, an amino acid analog, a proteinate, or an organic acid.

In further embodiments, the feed premix or feed supplement may further comprise one or more amino acids. Non-limiting suitable amino acids include standard amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), non-standard amino acids (e.g., L-DOPA, GABA, 2-aminobutyric acid, and the like), amino acid analogs, or combinations thereof. Amino acid analogs include α-hydroxy analogs (e.g., methionine hydroxy analog), as well side chain protected analogs or N-derivatized amino acids.

In alternate embodiments, the feed premix or feed supplement may further comprise one or more antioxidants. Suitable antioxidants include, but are not limited to, ascorbic acid and its salts, ascorbyl palmitate, ascorbyl stearate, anoxomer, n-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline (ethoxyquin), ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate, flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, n-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., lonox 100), 2,4-(tris-3',5'-bi-tert-butyl-4'-hydroxybenzyl)-mesitylene (i.e., lonox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or combinations thereof.

In still other embodiments, the feed premix or feed supplement may further comprise one or more organic acids. The organic acid may be a carboxylic acid or a substituted carboxylic acid. The carboxylic acid may be a mono-, di-, or tri-carboxylic acid. In general, the carboxylic acid may contain from about one to about twenty-two carbon atoms. Suitable organic acids, by way of non-limiting example, include acetic acid, adipic acid, butanoic acid, benzoic acid, cinnamaldehyde, citric acid, formic acid, fumaric acid, glutaric acid, glycolic acid, lactic acid, malic acid, mandelic acid, propionic acid, sorbic acid, succinic acid, tartaric acid, or combinations thereof. Salts of organic acids comprising carboxylic acids are also suitable for certain embodiments. Representative suitable salts include the ammonium, magnesium, calcium, lithium, sodium, potassium, selenium, iron, copper, and zinc salts of organic acids.

In yet other embodiments, the feed premix or feed supplement may further comprise one or more poly unsaturated fatty acids. Suitable poly unsaturated fatty acids (PUFAs) include long chain fatty acids with at least 18 carbon atoms and at least two carbon-carbon double bonds, generally in the cis-configuration. In specific embodiments, the PUFA may be an omega fatty acid. The PUFA may be an omega-3 fatty acid in which the first double bond occurs in the third carbon-carbon bond from the methyl end of the carbon chain (i.e., opposite the carboxyl acid group). Suitable examples of omega-3 fatty acids include all-cis 7,10,13-hexadecatrienoic acid; all-cis-9,12,15-octadecatrienoic acid (alpha-linolenic acid, ALA); all-cis-6,9,12,15,-octadecatetraenoic acid (stearidonic acid); all-cis-8,11,14,17-eicosatetraenoic acid (eicosatetraenoic acid); all-cis-5,8,11,14,17-eicosapentaenoic acid (eicosapentaenoic acid, EPA); all-cis-7,10,13,16,19-docosapentaenoic acid (clupanodonic acid, DPA); all-cis-4,7,10,13,16,19-docosahexaenoic acid (docosahexaenoic acid, DHA); all-cis-4,7,10,13,16,19-docosahexaenoic acid; and all-cis-6,9,12,15,18,21-tetracosenoic acid (nisinic acid). In an alternative embodiment, the PUFA may be an omega-6 fatty acid in which the first double bond occurs in the sixth carbon-carbon bond from the methyl end of the carbon chain. Examples of omega-6 fatty acids include all-cis-9,12-octadecadienoic acid (linoleic acid); all-cis-6,9,12-octadecatrienoic acid (gamma-linolenic acid, GLA); all-cis-11,14-eicosadienoic acid (eicosadienoic acid); all-cis-8,11,14-eicosatrienoic acid (dihomo-gamma-linolenic acid, DGLA); all-cis-5,8,11,14-eicosatetraenoic acid (arachidonic acid, AA); all-cis-13,16-docosadienoic acid (docosadienoic acid); all-cis-7,10,13,16-docosatetraenoic acid (adrenic acid); and all-cis-4,7,10,13,16-docosapentaenoic acid (docosapentaenoic acid). In yet another alternative embodiment, the PUFA may be an omega-9 fatty acid in which the first double bond occurs in the ninth carbon-carbon bond from the methyl end of the carbon chain, or a conjugated fatty acid, in which at least one pair of double bonds are separated by only one single bond. Suitable examples of omega-9 fatty acids include cis-9-octadecenoic acid (oleic acid); cis-11-eicosenoic acid (eicosenoic acid); all-cis-5,8,11-eicosatrienoic acid (mead acid); cis-13-docosenoic acid (erucic acid), and cis-15-tetracosenoic acid (nervonic acid). Examples of conjugated fatty acids include 9Z,11E-octadeca-9,11-dienoic acid (rumenic acid); 10E,12Z-octadeca-9,11-dienoic acid; 8E,10E,12Z-octadecatrienoic acid (α-calendic acid); 8E,10E,12E-octadecatrienoic acid (β-Calendic acid); 8E,10Z,12E-octadecatrienoic acid (jacaric acid); 9E,11E,13Z-octadeca-9,11,13-trienoic acid (α-eleostearic acid); 9E,11E,13E-octadeca-9,11,13-trienoic acid (β-eleostearic acid); 9Z,11Z,13E-octadeca-9,11,13-trienoic acid (catalpic acid), and 9E,11Z,13E-octadeca-9,11,13-trienoic acid (punicic acid).

In additional embodiments, the feed premix or feed supplement may further comprise one or more essential oils. Suitable essential oils include, but are not limited to, peppermint oil, cinnamon leaf oil, lemongrass oil, clove oil, castor oil, wintergreen oil, sweet orange, spearmint oil, cederwood oil, aldehyde C16, α terpineol, amyl cinnamic aldehyde, amyl salicylate, anisic aldehyde, benzyl alcohol, benzyl acetate, camphor, capsaicin, cinnamaldehyde, cinnamic alcohol, carvacrol, carveol, citral, citronellal, citronellol, p cymene, diethyl phthalate, dimethyl salicylate, dipropylene glycol, eucalyptol (cineole), eugenol, iso-eugenol, galaxolide, geraniol, guaiacol, ionone, listea cubea, menthol, menthyl salicylate, methyl anthranilate, methyl ionone, methyl salicylate, a phellandrene, pennyroyal oil, perillaldehyde, 1 or 2 phenyl ethyl alcohol, 1 or 2 phenyl ethyl propionate, piperonal, piperonyl acetate, piperonyl alcohol, D pulegone, terpinen 4 ol, terpinyl acetate, 4 tert butylcyclohexyl acetate, thyme oil, thymol, metabolites of trans-anethole, vanillin, ethyl vanillin, derivatives thereof, or combinations thereof.

In still other embodiments, the feed premix or feed supplement may further comprise one or more probiotics, prebiotics, or synbiotics (combination thereof). Probiotics and prebiotics include agents derived from yeast or bacteria that promote good digestive health. By way of non-limiting example, yeast-derived probiotics and prebiotics include yeast cell wall derived components such as β-glucans, arabinoxylan isomaltose, agarooligosaccharides, lactosucrose, cyclodextrins, lactose, fructooligosaccharides, laminariheptaose, lactulose, β-galactooligosaccharides, mannanoligosaccharides, raffinose, stachyose, oligofructose, glucosyl sucrose, sucrose thermal oligosaccharide, isomalturose, caramel, inulin, and xylooligosaccharides. In an exemplary embodiment, the yeast-derived agent may be β-glucans and/or mannanoligosaccharides. Sources for yeast cell wall derived components include *Saccharomyces bisporus, Saccharomyces boulardii, Saccharomyces cerevisiae, Saccharomyces capsularis, Saccharomyces delbrueckii, Saccharomyces fermentati, Saccharomyces lugwigii, Saccharomyces microellipsoides, Saccharomyces pastorianus, Saccharomyces rosei, Candida albicans, Candida cloaceae, Candida tropicalis, Candida utilis, Geotrichum candidum, Hansenula americana, Hansenula anomala, Hansenula wingei,* and *Aspergillus oryzae*. Probiotics and prebiotics may also include bacteria cell wall derived agents such as peptidoglycan and other components derived from gram-positive bacteria with a high content of peptidoglycan. Exemplary gram-positive bacteria include *Lactobacillus acidophilus, Bifedobact thermophilum, Bifedobat longhum, Streptococcus faecium, Bacillus pumilus, Bacillus subtilis, Bacillus licheniformis, Lactobacillus acidophilus, Lactobacillus casei, Enterococcus faecium, Bifidobacterium*

*bifidium, Propionibacterium acidipropionici, Propionibacteriium freudenreichii*, and *Bifidobacterium pseudolongum*.

In alternate embodiments, the feed premix or feed supplement may further comprise one or more enzymes or enzyme variants. Suitable non-limiting examples of enzymes include amylases, carbohydrases, cellulases, esterases, galactonases, galactosidases, glucanases, hemicellulases, hydrolases, lipases, oxidoreductases, pectinases, peptidases, phosphatases, phospholipases, phytases, proteases, transferases, xylanases, or combinations thereof.

In further embodiments, the feed premix or feed supplement may further comprise one or more herbals. Suitable herbals and herbal derivatives, as used herein, refer to herbal extracts, and substances derived from plants and plant parts, such as leaves, flowers and roots, without limitation. Non-limiting exemplary herbals and herbal derivatives include agrimony, alfalfa, aloe vera, amaranth, angelica, anise, barberry, basil, bayberry, bee pollen, birch, bistort, blackberry, black cohosh, black walnut, blessed thistle, blue cohosh, blue vervain, boneset, borage, buchu, buckthorn, bugleweed, burdock, capsicum, cayenne, caraway, cascara sagrada, catnip, celery, centaury, chamomile, chaparral, chickweed, chicory, chinchona, cloves, coltsfoot, comfrey, cornsilk, couch grass, cramp bark, culver's root, cyani, cornflower, damiana, dandelion, devils claw, dong quai, echinacea, elecampane, ephedra, eucalyptus, evening primrose, eyebright, false unicorn, fennel, fenugreek, figwort, flaxseed, garlic, gentian, ginger, ginseng, golden seal, gotu kola, gum weed, hawthorn, hops, horehound, horseradish, horsetail, hoshouwu, hydrangea, hyssop, iceland moss, irish moss, jojoba, juniper, kelp, lady's slipper, lemon grass, licorice, lobelia, mandrake, marigold, marjoram, marshmallow, mistletoe, mullein, mustard, myrrh, nettle, oatstraw, oregon grape, papaya, parsley, passion flower, peach, pennyroyal, peppermint, periwinkle, plantain, pleurisy root, pokeweed, prickly ash, psyllium, quassia, queen of the meadow, red clover, red raspberry, redmond clay, rhubarb, rose hips, rosemary, rue, safflower, saffron, sage, St. John's wort, sarsaparilla, sassafras, saw palmetto, scullcap, senega, senna, shepherd's purse, slippery elm, spearmint, spikenard, squawvine, stillingia, strawberry, taheebo, thyme, uva ursi, valerian, violet, watercress, white oak bark, white pine bark, wild cherry, wild lettuce, wild yam, willow, wintergreen, witch hazel, wood betony, wormwood, yarrow, yellow dock, yerba santa, yucca, or combinations thereof.

In still other embodiments, the feed premix or feed supplement may further comprise one or more natural pigments. Suitable pigments include, without limit, actinioerythrin, alizarin, alloxanthin, β-apo-2'-carotenal, apo-2-lycopenal, apo-6'-lycopenal, astacein, astaxanthin, azafrinaldehyde, aacterioruberin, aixin, α-carotine, β-carotine, γ-carotine, β-carotenone, canthaxanthin, capsanthin, capsorubin, citranaxanthin, citroxanthin, crocetin, crocetinsemialdehyde, crocin, crustaxanthin, cryptocapsin, α-cryptoxanthin, β-cryptoxanthin, cryptomonaxanthin, cynthiaxanthin, decaprenoxanthin, dehydroadonirubin, diadinoxanthin, 1,4-diamino-2,3-dihydroanthraquinone, 1,4-dihydroxyanthraquinone, 2,2'-diketospirilloxanthin, eschscholtzxanthin, eschscholtzxanthone, flexixanthin, foliachrome, fucoxanthin, gazaniaxanthin, hexahydrolycopene, hopkinsiaxanthin, hydroxyspheriodenone, isofucoxanthin, loroxanthin, lutein, luteoxanthin, lycopene, lycopersene, lycoxanthin, morindone, mutatoxanthin, neochrome, neoxanthin, nonaprenoxanthin, OH-Chlorobactene, okenone, oscillaxanthin, paracentrone, pectenolone, pectenoxanthin, peridinin, phleixanthophyll, phoeniconone, phoenicopterone, phoenicoxanthin, physalien, phytofluene, pyrrhoxanthininol, quinones, rhodopin, rhodopinal, rhodopinol, rhodovibrin, rhodoxanthin, rubixanthone, saproxanthin, semi-α-carotenone, semi-β-carotenone, sintaxanthin, siphonaxanthin, siphonein, spheroidene, tangeraxanthin, torularhodin, torularhodin methyl ester, torularhodinaldehyde, torulene, 1,2,4-trihydroxyanthraquinone, triphasiaxanthin, trollichrome, vaucheriaxanthin, violaxanthin, wamingone, xanthin, zeaxanthin, α-zeacarotene, or combinations thereof.

In additional embodiments, the feed premix or feed supplement may further comprise one or more nutritive agents. Nutritive agents provide calories and include carbohydrate sources, protein sources, fat sources, or combinations thereof. Carbohydrate sources may be of plant, microbial, or animal origin. Examples of suitable plant sources of carbohydrates include, without limit, grains such as wheat, oats, rice, rye, and so forth; legumes such as soy, peas, beans, and the like; corn; grasses; potatoes; vegetable plants; and plant fruits. The carbohydrate may be a monosaccharide such as pentose, glucose, galactose, and so forth; a disaccharide such as sucrose, lactose, maltose, and the like; an oligosaccharide such as a fructo-oligosaccharide, galactose-oligosaccharide, mannan-oligosaccharide, etc.; or a polysaccharide such as starch, glycogen, cellulose, arabinoxylan, pectin, gum, chitins, and so forth. Protein sources may be derived from a plant. Non-limiting examples of suitable plants that provide a good source of protein include amaranth, arrowroot, barley, buckwheat, canola, cassava, channa (garbanzo), legumes, lentils, lupin, maize, millet, oat, pea, potato, rice, rye, sorghum, soybean, sunflower, tapioca, triticale, wheat, seagrasses, and algae. Alternatively, the protein source may be derived from an animal. For example, the animal protein source may be derived from a dairy product, bird eggs, or from the muscles, organs, connective tissues, or skeletons of land-based or aquatic animals. Fat sources may be of plant, animal, or microbial origin. Non-limiting examples of plant derived fats include vegetable oils (e.g., canola oil, corn oil, cottonseed oil, palm oil, peanut oil, safflower oil, soybean oil, and sunflower oil) and oilseeds (e.g., canola seeds, cottonseeds, flax seeds, linseeds, Niger seeds, sesame seeds, soy beans, and sunflower seeds), distillers grains, or algae. Animal derived fats include, without limit, fish oils (e.g., menhaden oil, anchovy oil, albacore tuna oil, cod liver oil, herring oil, lake trout oil, mackerel oil, salmon oil, and sardine oil), high fat fish meal (e.g., menhaden meal, anchovy meal, herring meal, pollack meal, salmon meal, tuna meal, and whitefish meal), and animal fats (e.g., poultry fat, beef tallow, butter, pork lard, and whale blubber).

In yet other embodiments, the feed premix or feed supplement may further comprise one or excipients. Suitable excipients include binders and fillers. Examples of suitable binders include, without include, without limit, starches (e.g., corn starch, potato starch, wheat starch, rice starch, and the like), pregelatinized starch, hydrolyzed starch, cellulose, microcrystalline cellulose, cellulose derivatives (e.g., methylcellulose, ethylcellulose, hydroxypropylcellulose, hydroxypropylmethylcellulose, sodium carboxymethylcellulose, and the like), saccharides (e.g., sucrose, lactose, and so forth), sugar alcohols (e.g., maltitol, sorbitol, xylitol, polyethylene glycol, and the like), alginates (e.g., alginic acid, alginate, sodium alginate, and so forth), gums (e.g., gum arabic, guar gum, gellan gum, xanthan gum, and the like), pectins, gelatin, $C_{12}$-$C_{18}$ fatty acid alcohols, polyvinylpyrrolidinone (also called copovidone), polyethylene oxide, polyethylene glycol, polyvinyl alcohols, waxes (e.g., candelilla wax, carnauba wax, beeswax, and so forth), or combinations of any of the foregoing. Non-limiting examples of suitable fillers (also called diluents) include cellulose, microcrystalline cellulose, cellulose ethers (e.g., ethyl cellulose, methyl cellulose, hydroxypropyl cellulose, hydroxypropyl methylcellulose, sodium carboxymethylcellulose, etc.), cellulose esters (e.g., cellulose acetate, cellulose butyrate, and mixtures thereof), starches (e.g., corn starch, rice starch, potato starch, tapioca starch, and the like), modified starches, pregelatinized starches, phosphated starches, starch-lactose, starch-calcium carbonate, sodium starch glycolate, glucose, fructose, sucrose, lactose, xylose, lactitol, mannitol, malitol, sorbitol, xylitol, maltodextrin, trehalose, calcium carbonate, calcium sulfate, calcium phosphate, calcium silicate, magnesium carbonate, magnesium oxide, talc, or combinations thereof.

Definitions

The following definitions are provided to facilitate understanding of the disclosure.

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "about," particularly in reference to a given quantity, is meant to encompass deviations of plus or minus five percent.

As used herein, the term "aliphatic" refers to a hydrocarbyl group in which the carbon atoms are linked in open chains, i.e., either linear or branched but not cyclic. Alkyl, alkenyl, and alkynyl groups, optionally substituted, are aliphatic.

The term "alkyl" as used herein describes groups containing from one to thirty carbon atoms in the principal chain. They may be straight or branched chain or cyclic and include methyl, ethyl, propyl, isopropyl, butyl, hexyl and the like.

The term "alkenyl" as used herein describes groups containing from two to thirty carbon atoms in the principal chain and further comprising at least one carbon-carbon double bond. They may be straight or branched chain or cyclic and include ethenyl, propenyl, isopropenyl, butenyl, isobutenyl, hexenyl, and the like.

As used herein, the term "methionine equivalent" refers to the sum of L-methionine, D-methionine, and derivatives 2-hydroxy-4-methylthio-butanoic acid measured in a sample and reflects the amount of available methionine.

EXAMPLES

The following examples illustrate various embodiments of the present disclosure.

Example 1: In Vitro Evaluation of Rumen Protection

Degradation of ester and other derivatives 2-hydroxy-4-methylthio-butanoic acid (HMTBa) by rumen microorganisms was tested in vitro. Schematics of the HMTBa derivatives are presented below in Table. 1.

TABLE 1

HMTBa derivatives

A. HMTBa Cyclic Dimer, 3,6-bis(2-methylthio)ethyl-1,4-dioxane-2,5-dione

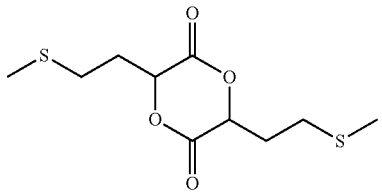

B. Alpha C14 Ester, a mixture of alpha C14 esters with 1-5 HMTBa units, and approximately 5-10% free HMTBA

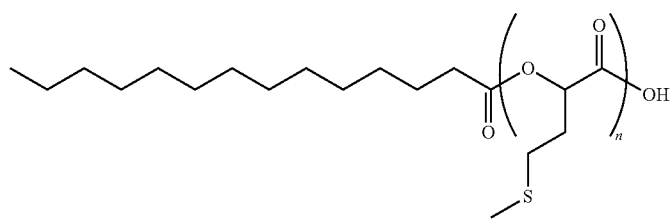

n = 1-5

C. Hydroxy C18 Ester, a mixture of hydroxy C18 esters with 1-3 HMTBa units

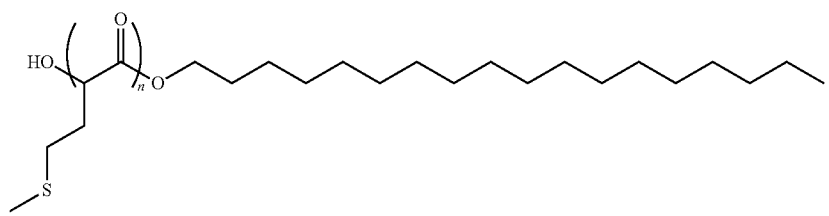

TABLE 1-continued

HMTBa derivatives n = 1-3
D. Alpha C18 Ester, a mixture of alpha 18 esters with 1-5 HMTBa units

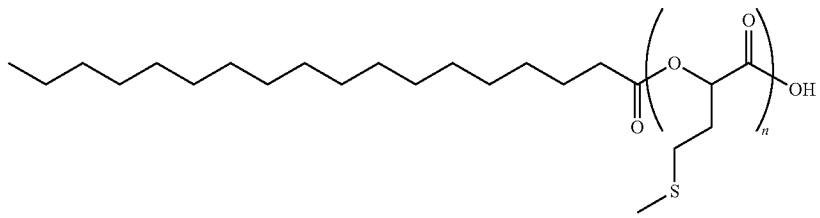

n = 1-5
E. HMTBa Oligomer, a polymer of approximately 7 HMTBa units with an average molecular weight of ~1000. Formulation is 40% oligomer on a silica carrier

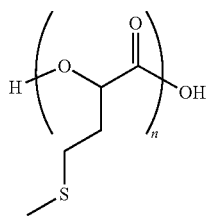

n = average of 7 HMTBA units

Following the methodology of Patterson and Kung (J. Dairy Sci., 1988, vol. 71, pp. 3292-3301), fermentation substrate comprising casein, cellobiose, starch, pectin, and cellulose was added at a rate of 0.45 g to 250 mL fermentation flasks. HMTBa derivatives were randomly assigned to flasks and thoroughly mixed to ensure that all compounds were incorporated into the substrate. Methionine hydroxy analog (MHA), polymer encapsulated methionine (eMet) were also included as controls, as well as a blank. Details about the compounds are provided in Table 2. A total of 28 fermentation flasks were used, resulting in 4 replicates per treatment for each of the two experiments.

TABLE 2

Composition of Compounds Tested

| Compound | Active | Active, % | Compound inclusion, g | Active inclusion, g |
|---|---|---|---|---|
| Cyclic Dimer | HMTBa | 100 | 0.10 | 0.1014 |
| α C14 Ester | HMTBa | 41.4 | 0.24 | 0.1002 |
| OH C18 Ester | HMTBa | 37.3 | 0.27 | 0.1015 |
| α C18 Ester | HMTBa | 21.6 | 0.46 | 0.0993 |
| Oligomer | HMTBa | 42.5[1] | 0.10 | 0.0429 |
| MHA | HMTBa | 86.0 | 0.12 | 0.1052 |
| eMet | Methionine | 73.6 | 0.13 | 0.0964 |

[1] Analysis after the completion of the experiment revealed that the starting concentration of active was much less than previously calculated due to inclusion of a silica carrier.

Three cannulated Holstein steers were utilized as rumen fluid donors. Steers were housed on pasture, allowed to graze freely, and provided free choice supplement. Approximately 1000 mL of rumen fluid and a handful of rumen contents were obtained from each steer. Rumen fluid and contents were combined in pre-heated thermoses, transported to the lab, blended using a hand blender, and strained through 8 layers of cheese cloth. Combined rumen fluid was maintained under $CO_2$ and thoroughly mixed. Rumen fluid (100 mL) was added to each fermentation flask (ANKOM RF Gas Production System; ANKOM Technology, Macedon, N.Y.) under $CO_2$, sealed, and placed into a pre-warmed (39° C.) water bath. The ANKOM RF Gas Production System was enabled and measured pressure every 10 minutes.

Fermenter fluid was sampled at 1, 3, 6, and 12 h to determine the degradation of the compounds. Fluid was sampled using a 16 G, 1.5 inch needle piercing the side arm septum of the fermentation flask. A 5 mL syringe was attached to the needle and as the flask was titled and gently swirled, approximately 5 mL of fluid was subsampled at each timepoint. A fresh syringe and needle was used for every flask at every timepoint to minimize carryover. Following sampling, fluid was transferred to a 15 mL conical tube, acidified with 1 mL of 25% m-phosphoric acid, and centrifuged at 3,000×g for 10 minutes at 4° C. Following centrifugation, the supernatant was harvested, and syringe filtered (0.45 μm) to obtain 1.5 mL of filtered supernatant. Samples were filtered into microcentrifuge tubes and stored at −20° C. until analysis. Standard LC-MS/MS procedures were employed to analyze the levels of free HMTBa or free methionine in the final filtered supernatants.

Due to variability associated with in vitro methodology, replicates were evaluated for similarity. In situations where the replicates had a coefficient of variation greater than 15%, had one of the replicate samples removed to reduce the coefficient of variation below 15%. As a result, three samples were removed from the data set from experiment 1, and seven samples were removed in experiment 2. Recovery of HMTBa or methionine was determined and expressed relative to initial amount of HMTBA or methionine (active) added. This was then used to estimate ruminal undegradability of the compounds by subtracting the value from 1.

The following equation was used to determine the ruminal undegradability of HMTBa products:

$$\text{Ruminal undegradability} = 1 - \frac{\text{Recovered free } HMTBa, \text{ ppm}}{\text{Initial } HMTBa \text{ inclusion, ppm}}$$

The following equation was used to determine the ruminal undegradability of methionine products:

$$\text{Ruminal undegradability} = 1 - \frac{\text{Recovered free methionine, ppm}}{\text{Initial methionine inclusion, ppm}}$$

Hourly pressure measurements from the Gas Production System were recorded and converted from psi to mL of gas using the Ideal Gas Law and Avogadro's Law. Data were analyzed using the MIXED procedure of SAS® and significance declared at $P \leq 0.05$.

Free HMTBa or methionine, i.e., HMTBA or methionine not bound to any molecule in rumen fluid, was recovered following in vitro incubation and the levels (ppm) are presented in Table 3. These values were used to determine the estimated ruminal undegradability of the various compounds, which are shown in Table 4.

TABLE 3

Free Active Recovered after 12 hr of in vitro Incubation

| Compound tested | Free Active, ppm | |
|---|---|---|
| | Experiment 1 | Experiment 2 |
| α C14 Ester | 93.16$^a$ | — |
| OH C18 Ester | 0.00$^b$ | 14.00$^a$ |
| α C18 Ester | — | 121.33$^b$ |
| Cyclic Dimer | 439.6$^c$ | — |
| Oligomer | 136.1$^d$ | — |
| MHA | 623.5$^e$ | 828.4$^c$ |
| eMet | 0.00$^b$ | 0.00$^a$ |
| SE | 8.44 | 16.3 |
| P-value | <0.0001 | <0.0001 |

$^{abcde}$Means within a column without a common superscript differ (P ≤ 0.05).

TABLE 4

Estimated Ruminal Stability Following 12 hours of in vitro Incubation

| Compound tested | Ruminal undegradability | |
|---|---|---|
| | Experiment 1 | Experiment 2 |
| α C14 Ester | 90.71$^a$ | — |
| OH C18 Ester | 100.0$^b$ | 98.61$^a$ |
| α C18 Ester | — | 87.79$^b$ |
| Cyclic Dimer | 56.64$^c$ | — |
| Oligomer | 68.30$^d$ | — |
| MHA | 40.69$^e$ | 19.73$^c$ |
| eMet | 100.0$^b$ | 100.0$^a$ |
| SE | 0.95 | 1.6 |
| P-value | <0.0001 | <0.0001 |

$^{abcde}$Means within a column without a common superscript differ (P ≤ 0.05).

When the free HMTBa or methionine recovered is considered following 12 h of incubation, close to the 16 h benchmark traditionally used with in situ evaluation of rumen protected product, the ranking of products for the lowest release in experiment 1 is as follows: eMet=hydroxy C18 ester<alpha C14 ester<oligomer<cyclic dimer<MHA. This ranking is the same for estimated ruminal undegradability of compounds tested in experiment 1 (eMet=hydroxy C18 ester>alpha C14 ester>oligomer>cyclic dimer>MHA).

When the free HMTBa or methionine recovered is considered following 12 h of incubation, close to the 16 h benchmark traditionally used with in situ evaluation of rumen protected product, the ranking of products for the lowest release in experiment 2 is as follows: eMet=hydroxy C18 ester<alpha C18 ester<MHA. This ranking is the same for estimated ruminal undegradability of prototypes tested in experiment 2 (eMet=hydroxy C18 ester<alpha C18 ester<MHA).

Gas production was also measured during the incubations to ensure that the microbial population was active. Results are shown in Table 5 (experiment 1) and Table 6 (experiment 2). As expected, the amount of gas produced increased over time suggesting that the microbial population was active. Lack of differences between treatments at all time points further suggests that the estimated undegradability values obtained from this experiment were not biased by the activity of the microbial population.

TABLE 5

Gas Produced During Experiment 1.

| Compound tested | Gas, mL | | | |
|---|---|---|---|---|
| | 1 h | 3 h | 6 h | 12 h |
| α C14 Ester | 20.93 | 64.76 | 99.18 | 122.1 |
| OH C18 Ester | 23.89 | 59.49 | 94.63 | 103.5 |
| Cyclic dimer | 24.68 | 69.16 | 105.4 | 129.9 |
| Oligomer | 21.95 | 68.13 | 83.26 | 131.0 |
| MHA | 22.41 | 60.40 | 122.2 | 138.5 |
| eMet | 27.75 | 74.46 | 109.0 | 130.1 |
| SE | 3.30 | 6.70 | 17.67 | 17.46 |
| P-value | 0.8091 | 0.5978 | 0.5527 | 0.5415 |

TABLE 6

Gas Produced During Experiment 2.

| Compound tested | Gas, mL | | | |
|---|---|---|---|---|
| | 1 h | 3 h | 6 h | 12 h |
| OH C18 Ester | 2.98 | 30.48 | 47.68 | 67.15 |
| α C18 Ester | 2.90 | 40.95 | 57.05 | 75.62 |
| MHA | 2.24 | 20.25 | 40.49 | 65.86 |
| eMet | 2.34 | 31.85 | 44.02 | 69.72 |
| SE | 0.69 | 8.46 | 8.36 | 11.8 |
| P-value | 0.8029 | 0.3756 | 0.4981 | 0.9221 |

The experiments described in this example show that hydroxy C18 ester, alpha C 18 ester, and alpha C14 ester provided greater than 80% ruminal undegradability after 12 h of incubation. Though slightly less, HMTBA oligomer also provides 68% ruminal undegradability. This suggests that chemical linkage between a long chain fatty acid and HMTBa provides rumen protection for HMTBa.

Example 2. In Vivo Evaluation of Rumen Protection

An in vivo steer experiment was conducted as a randomized complete block design over a 14-day period. The experiment consisted of 4 treatments with 5 steers per treatment. The first 6 days of the experiment served as an adaptation period to the basal diet, while day 7 through 14 served as the observational period where treatments were administered. All steers were individually housed in the intensive area of a research farm (Montgomery City, Mo.)

for the duration of the trial and allowed ad libitum access to water. A common TMR was offered at a rate of 11.6 kg per day (as-is basis; Table 7) for the duration of the experiment.

TABLE 7

Experimental Diet Fed To All Steers Throughout The Experiment

| Ingredients | Amount (%, DM) | Amount (kg, as-is) |
|---|---|---|
| Cattle Pellet, 14% commodity | 50 | 5.50 |
| Chopped Grass Hay | 22.5 | 2.75 |
| Alfalfa Hay | 22.5 | 2.75 |
| Chopped Wheat Straw | 5.0 | 0.60 |

The products utilized in this experiment are summarized in Table 8. Briefly, MHA, a source of HMTBa with 40% ruminal bypass, and polymer encapsulated methionine (eMet), a source of D,L-methionine with 90% ruminal bypass served as controls for esters of HMTBA, e.g., alpha C14 ester and hydroxy C18 ester (see Table 1 above). Inclusion rates of products varied to allow for all treatments to provide approximately 43 g of active (HMTBa or Methionine). Individual products were mixed with ground corn so that 250 g of the mixes could be delivered to each steer. Starting on d 7 of the experiment, the ground corn mixes were top dressed on the TMR to allow for full consumption by the steers (usually consumed in less than 30 minutes after feed delivery). Top dressing with the ground mixes occurred daily through d 14 (conclusion of the experiment).

TABLE 8

Products Used in vivo Study

| | Product Supplemented | | | |
|---|---|---|---|---|
| | MHA | α C14 Ester | OH C18 Ester | eMet |
| Active molecule | HMTBa | HMTBa | HMTBa | Methionine |
| Percent active | 84.0 | 36.2 | 39.3 | 73.6 |
| Product inclusion, g | 51.4 | 119.2 | 110.0 | 58.6 |
| Active inclusion, g | 43.18 | 43.17 | 43.23 | 43.13 |

Individual feed intake (as-fed) was recorded daily. Samples of the diet (~250 g) were taken on day 0, 7 and 17 of the experiment and saved for future analysis. Steers' body weights were recorded on day 0, 6, and 14 of the trial.

On days, 5, 6, 13, and 14, blood was collected from the coccygeal vein of all steers 0, 2, 4, and 6 h after feeding (0700, 0900, 1100, 1300 h). Blood was collected in sodium heparin filled tubes (BD Vacutainer; Franklin Lakes, N.J.) and stored on ice until centrifugation. Samples were centrifuged after each collection time, at 2,000×g at 4° C. for 15 minutes. Following centrifugation, plasma was aliquoted into 3 sub-samples by day through addition of 400 μL of plasma to the corresponding aliquot for that experimental day. This resulted in a pooled sample for each steer for each of the following days: 5, 6, 13, and 14. After each sample time and prior to analysis, plasma aliquots were stored at −20° C. Samples were analyzed for L-methionine, D-methionine, and HMTBa via HPLC with MS detection.

Daily individual feed intake was reduced to weekly average for each steer for use in statistical analysis. To compare across different actives, concentration of L-methionine, D-methionine, and HMTBa were summed to generate a methionine equivalent value. This value represents the potential for D-methionine and HMTBa to be converted to L-methionine and be used by the steer. Plasma data from day 5 and 6 were averaged across day for each measure and used as a covariate. Data was analyzed using the MIXED procedure of SAS® with repeated measures. Mean separation was done using a Tukey's adjustment and significance declared at $P \leq 0.05$.

No effect of methionine source was observed on BW or feed intake (Table 9). The ability of the different sources of methionine to enrich plasma methionine concentrations are shown in Table 10.

TABLE 9

Effect of Source of Methionine on Body Weight and Feed Intake

| | Product Supplemented | | | | | |
|---|---|---|---|---|---|---|
| | MHA | α C14 Ester | OH C18 Ester | eMet | SE | P-value |
| Body weight, kg | 503.3 | 507.7 | 512.6 | 507.9 | 3.9 | 0.4216 |
| Feed Intake, kg as-fed | 11.4 | 11.2 | 11.6 | 11.5 | 0.13 | 0.3085 |

TABLE 10

Effect of Source of Methionine on Plasma concentrations of L-Methionine, D-Methionine or HMTBa

| μg/mL in Plasma | Product Supplemented | | | | | |
|---|---|---|---|---|---|---|
| | MHA | α C14 Ester | OH C18 Ester | eMet | SE | P-value |
| L-methionine | $5.312^a$ | $5.206^a$ | $6.503^b$ | $7.061^b$ | 0.3352 | 0.0003 |
| D-methionine | $0.000^a$ | $0.000^a$ | $0.000^a$ | $1.080^b$ | 0.0949 | <0.0001 |
| HMTBa | $0.324^a$ | $0.288^a$ | $0.689^b$ | $0.000^c$ | 0.0718 | <0.0001 |
| Methionine equivalents[1] | $5.666^a$ | $5.453^a$ | $7.197^b$ | $8.149^b$ | 0.4094 | <0.0001 |

[1] Methionine equivalents is the sum of L-methionine, D-methionine, and HMTBa to reflect the potential supply of methionine to the steer.

These data show that L-methionine concentration was highest (P=0.0003) with eMet and hydroxy C18 ester compared to alpha C14 ester and MHA. Concentration of D-methionine was highest (P<0.0001) with eMet as compared to hydroxy C18 ester, alpha C 14 ester and MHA which all had undetectable levels of D-methionine. Plasma HMTBa was highest (P<0.0001) with hydroxy C18 ester when compared to alpha C14 ester and MHA, while eMet had the lowest concentration (P<0.0001) as it was undetectable in this treatment. Lack of detecting D-methionine in plasma of steers supplemented products containing HMTBa is understandable as these steers were not supplemented with a source of D-methionine. Conversely, lack of detecting HMTBa in plasma of steers supplemented eMet is also understandable as these steers were not supplemented a HMTBa source. This supports the conclusion that all steers consumed their respective treatments. When methionine equivalents, the sum of L-methionine, D-methionine, and HMTBa, was calculated eMet and hydroxy C18 ester had greater concentrations (P<0.0001) than alpha C14 ester or MHA. When comparing methionine equivalents, eMet enriched plasma at 1.5 times that of MHA, while hydroxy C18 ester enriched plasma at 1.3 times that of MHA.

These data indicated that the ranking of these methionine products based on their contribution to plasma methionine equivalent pool is: eMet=hydroxy C18 ester>MHA=alpha C14 ester. This suggests that hydroxy C18 ester of HMTBa is efficacious in delivering a methionine source to the small intestine for absorption that can lead to increases in milk protein.

What is claimed is:

1. A method for increasing rumen bypass of methionine hydroxy analog in a ruminant, the method comprising administering to the ruminant a compound of Formula (I) or Formula (II):

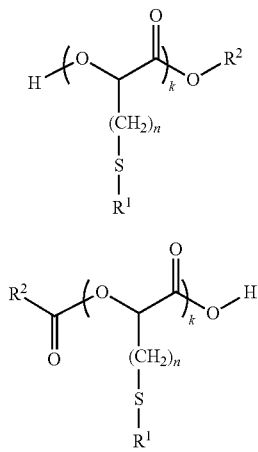

wherein:
R$^1$ is methyl;
R$^2$ is C$_{12}$ to C$_{30}$ alkyl or C$_{12}$ to C$_{30}$ alkenyl;
n is 2;
k is from 1 to 10; and
the increase in rumen bypass upon administration of the compound of Formula (I) or Formula (II) is relative to administration of 2-hydroxy-4-methylthio-butanoic acid, and the rumen bypass of the compound of Formula (I) or Formula (II) is at least 75%.

2. The method of claim 1, wherein R$^2$ is C$_{14}$ alkyl or alkenyl, C$_{16}$ alkyl or alkenyl, C$_{18}$ alkyl or alkenyl, C$_{20}$alkyl or alkenyl, C$_{22}$ alkyl or alkenyl, C$_{24}$ alkyl or alkenyl, or C$_{26}$ alkyl or alkenyl.

3. The method of claim 2, wherein R$^2$ is C$_{16}$ alkyl or alkenyl, C$_{18}$ alkyl or alkenyl, or C$_{20}$alkyl or alkenyl.

4. The method of claim 1, wherein the rumen bypass of the compound of Formula (I) or Formula (II) is at least 85%.

5. The method claim 1, wherein the compound of Formula (I) or Formula (II) is provided to the ruminant as part of its feed ration, as a feed premix, or a feed supplement.

6. The method of claim 1, wherein the ruminant is chosen from dairy cattle, beef cattle, sheep, or goat.

7. The method of claim 1, wherein the ruminant is a dairy cow.

8. A method for increasing methionine hydroxy analog provided to a ruminant's small intestine for absorption by increasing rumen bypass of the methionine hydroxy analog, the method comprising administering to the ruminant an effective amount of a compound of Formula (I) or Formula (II):

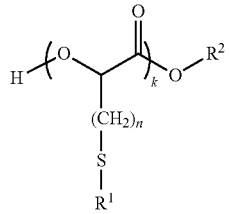

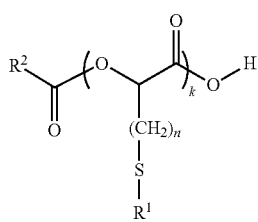

wherein:
R$^1$ is methyl;
R$^2$ is C$_{12}$ to C$_{30}$ alkyl or C$_{12}$ to C$_{30}$ alkenyl;
n is 2;
k is from 1 to 10, and
the increase in methionine hydroxy analog provided to the ruminant's small intestine and the increase in rumen bypass upon administration of the compound of Formula (I) or Formula (II) are relative to administration of 2-hydroxy-4-methylthio-butanoic acid, and the rumen bypass of the compound of Formula (I) or Formula (II) is at least 75%.

9. The method of claim 8, wherein R$^2$ is C$_{14}$ alkyl or alkenyl, C$_{16}$ alkyl or alkenyl, C$_{18}$ alkyl or alkenyl, C$_{20}$alkyl or alkenyl, C$_{22}$ alkyl or alkenyl, C$_{24}$ alkyl or alkenyl, or C$_{26}$ alkyl or alkenyl.

10. The method of claim 9, wherein R$^2$ is C$_{16}$ alkyl or alkenyl, C$_{18}$ alkyl or alkenyl, or C$_{20}$alkyl or alkenyl.

11. The method of claim 8, wherein the compound of Formula (I) or Formula (II) is protected from degradation by rumen microorganisms.

12. The method of claim 8, wherein the rumen bypass of the compound of Formula (I) or Formula (II) is at least 85%.

13. The method claim 8, wherein the compound of Formula (I) or Formula (II) is provided to the ruminant as part of its feed ration, as a feed premix, or a feed supplement.

14. The method of claim 8, wherein the ruminant is chosen from dairy cattle, beef cattle, sheep, or goat.

15. The method of claim 8, wherein the ruminant is a dairy cow.

* * * * *